United States Patent
Manikandan et al.

(10) Patent No.: US 8,766,014 B2
(45) Date of Patent: Jul. 1, 2014

(54) HETEROGENEOUS CATALYSTS

(75) Inventors: Palanichamy Manikandan, Pune (IN); Sreenivasa Rao, Pune (IN); Phani Kiran Bollapragada, Pune (IN)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 13/825,610

(22) PCT Filed: Sep. 26, 2011

(86) PCT No.: PCT/US2011/053206
§ 371 (c)(1),
(2), (4) Date: Mar. 22, 2013

(87) PCT Pub. No.: WO2012/050807
PCT Pub. Date: Apr. 19, 2012

(65) Prior Publication Data
US 2013/0190537 A1     Jul. 25, 2013

Related U.S. Application Data

(60) Provisional application No. 61/391,742, filed on Oct. 11, 2010.

(51) Int. Cl.
*C07C 45/49* (2006.01)
*C07C 29/36* (2006.01)

(52) U.S. Cl.
USPC .......................................... 568/451; 568/909

(58) Field of Classification Search
USPC ................................. 568/451, 909
See application file for complete search history.

(56) References Cited

U.S. PATENT DOCUMENTS

| | | | |
|---|---|---|---|
| 4,361,711 A | 11/1982 | Blaskie et al. | |
| 4,492,773 A | 1/1985 | Ball et al. | |
| 4,652,539 A | 3/1987 | Alvila et al. | |
| 4,758,600 A | 7/1988 | Arimitsu et al. | |
| 5,409,877 A | 4/1995 | Takeuchi et al. | |

FOREIGN PATENT DOCUMENTS

| | | |
|---|---|---|
| GB | 1012011 A | 12/1965 |
| GB | 1129809 A | 10/1968 |
| GB | 2171925 A | 9/1986 |
| WO | 0001651 A1 | 1/2000 |
| WO | 0248039 A1 | 6/2002 |

OTHER PUBLICATIONS

Steven S. C. Chuang et al., in "Role of Silver Promoter in Carbon Monoxide Hydrogenation and Ethylene Hydroformylation over Rh/SiO2 Catalysts", Journal of Catalysis, 138, 536-546 (1992).
Steven S. C. Chuang et al., in "C2 Oxygenate Synthesis from CO Hydrogenation on AgRh/SiO2", Applied Catalysis, vol. 57, pp. 241-251, 1990.
PCT/US2011/053206; International Search Report and Written Opinion of the International Searching Authority; Jan. 20, 2012.
PCT/ US2011/053206, International Preliminary Report on Patentability, Sep. 10, 2012.

*Primary Examiner* — Sikarl Witherspoon

(57) ABSTRACT

Convert a mixture of synthesis gas and ethylene to a product stream that contains at least one C3 oxygenate using a supported, heterogeneous catalyst represented by formula $Rh_aAg_bSn_cX_dY_eO_x$. In the formula, X is at least one transition element other than rhodium or silver, and Y is at least one element selected from alkali metals and alkaline earth metals.

3 Claims, No Drawings

HETEROGENEOUS CATALYSTS

This application is a non-provisional application claiming priority from the U.S. Provisional Patent Application No. 61/391,742, filed on Oct. 11, 2010, entitled "HETEROGENEOUS CATALYSTS" the teachings of which are incorporated by reference herein, as if reproduced in full hereinbelow.

This invention relates to a process for converting a feedstream of ethylene and synthesis gas ("syngas", a mixture of carbon monoxide (CO) and hydrogen ($H_2$)) to a product stream that comprises at least one three carbon ($C_3$) oxygenate (e.g. propionaldehyde or propanol) using a heterogeneous catalyst that comprises a combination of metals on a catalyst support.

Steven S. C. Chuang et al., in "Role of Silver Promoter in Carbon Monoxide Hydrogenation and Ethylene Hydroformylation over $Rh/SiO_2$ Catalysts", *Journal of Catalysis*, 138, 536-546 (1992), teach that silver (Ag) increases selectivity and rate of formation for acetaldehyde (a two carbon atom ($C_2$) oxygenate) during CO hydrogenation and for propionaldehyde during ethylene hydroformylation on a silica ($SiO_2$)-supported rhodium (Rh) catalyst. They also teach that certain promoters, such as manganese (Mn), zirconium (Zr), titanium (Ti), vanadium (V) and lanthanum (La) oxides as well as alkali metals, are known to enhance $C_2$ oxygenate selectivity, while other promoters, including zinc (Zn) and iron (Fe), modify catalyst activity by blocking surface sites.

Steven S. C. Chuang et al., in "$C_2$ Oxygenate Synthesis from CO Hydrogenation on $AgRh/SiO_2$", *Applied Catalysis*, volume 57, pages 241-251, notes that Ag decreases rates of formation for methane and $C_{2+}$ hydrocarbons more than those for $C_2$ oxygenates, resulting in a marked increase in $C_2$ oxygenate selectivity.

U.S. Pat. No. 4,492,773 (Ball et al.) teaches production of $C_1$ to $C_4$ oxygenates by contacting syngas at a temperature within a range of 150 degrees Celsius (° C.) to 450° C. and a pressure within a range of from 1 bar (100 kilopascals (KPa) to 700 bars (70,000 KPa) with a catalyst comprising a supported mixture of a Rh component and an Ag component. Other metal components that may be incorporated include iron (Fe), Mn, Mo, tungsten (W), ruthenium (Ru), chromium (Cr), thorium (Th) and zirconium (Zr). Support materials include silica, alumina, silica/alumina, magnesia, thoria, titania, chromia, zirconia, and active carbon. The catalyst support may be activated with one or more metal or non-metal activator components selected from alkali metals, Th, Mn, Rh, Fe, Cr, Mo, Zr, rhenium (Re), Ag, boron (B) and phosphorous (P).

In some aspects, this invention is a process for converting a feedstream comprising syngas and ethylene to a product stream that comprises at least one three carbon oxygenate, which process comprises placing the feedstream in contact with a heterogeneous catalyst under conditions sufficient to effect conversion of the feedstream to the product stream, the catalyst comprising a combination of metals on a catalyst support, the combination of metals being represented by general formula $Rh_aAg_bSn_cX_dY_eO_x$ wherein X is at least one transition element other than rhodium or silver, Y is at least one element selected from alkali metals and alkaline earth metals, a is a real number within a range of from 0.1 millimoles per hectogram (mmol/hg) to 50 mmol/hg, b is a real number within a range of from 0.1 mmol/hg to 50 mmol/hg, c is a real number within a range of from 0.1 mmol/hg to 50 mmol/hg, d is a real number within a range of from 0 mmol/hg to 250 mmol/hg, e is a real number within a range of from 0 mmol/hg to 1500 mmol/hg, and x is a real number greater than zero needed to balance the total charges of Rh, Ag, Sn, X and Y elements, the catalyst support being at least one of silica, alumina, titania, magnesia, magnesium aluminate, and zinc aluminate.

The combination of metals represented by the above general formula comprises, consists essentially of, or consists of Rh, Ag, and tin (Sn), optionally in further combination with at least one promoter selected from X (at least one transition metal other than silver or rhodium) when d is greater than 0 and Y (at least one alkali metal or alkaline earth metal) when e is greater than 0. When d, e or both d and e are 0, the corresponding element (X for d and Y for e) is absent from the combination of metals.

The process conditions for conversion of the feedstream to the product stream include at least one of a pressure within a range of from 12 pounds per square inch gauge (psig) (82.7 kilopascals (KPa)) to 4,000 psig (27.6 megapascals (MPa)), preferably from 20 bars (2 MPa) to 45 bar (4.5 MPa), a temperature of from 100° C. to 450° C., preferably from 280° C. to 320° C., a gas hourly space velocity (GHSV) within a range of from 25 reciprocal hours ($h^{-1}$) to 25,000 $h^{-1}$, preferably from 2000 $h^{-1}$ to 10000 $h^{-1}$, and a feedstream ratio of ethylene to carbon monoxide to hydrogen ($C_2H_4:CO:H_2$) within a range of from 0.01:10:10 to 10.0:0.01:0.01, with a ratio of 1:1:1 yielding very satisfactory results.

The transition metals other than Rh and Ag are selected from a group consisting of elements 21 through 29 (scandium (Sc) through Cu, elements 39 (yttrium (Y)) through 44 (ruthenium (Ru)), 46 (palladium (Pd), 57 through 79 (lanthanum (La) through Au) and all known elements from 89 (actinium (Ac)) on as such elements are listed in The Periodic Table of the Elements (inside cover of *Hawley's Condensed Chemical Dictionary, Twelfth Edition* (1993)). Preferred transition metals include Zn, Fe, Cr, Co, and Ir.

The alkali metals include sodium (Na), lithium (Li), potassium (K), rubidium (Rb), cesium (Cs) and francium (Fr). The alkaline earth metals include magnesium (Mg), beryllium (Be), calcium (Ca), strontium (Sr), barium (Ba) and radium (Ra). When the catalyst includes component Y, one may use at least alkali metal, or at least one alkaline earth metal or a combination of at least one alkali metal and at least one alkaline earth metal.

The catalyst support is at least one of silica, alumina, titania, magnesia, magnesium aluminate, magnesium-modified silica, magnesium-modified alumina, zirconium-modified silica, zirconium-modified alumna, zinc-modified silica, zinc-modified alumina, and zinc aluminate, with silica, magnesia, magnesium aluminate and alumina being preferred supports.

As an additional option, one may admix an alkali metal carbonate such as sodium carbonate with catalyst compositions represented by the above general formula.

The alkali metal carbonate appears to reduce catalyst acidity, a possible explanation for a reduced tendency to promote hydrogenation of alkenes to alkenes during the process of at least some aspects of this invention.

The process of at least some aspects of this invention has utility in producing at least one $C_3$ oxygenate. The $C_3$ oxygenates, in turn have utility in serving as feedstocks for production of other chemicals such as production of propylene by dehydration of propanol. Propylene, in turn, has utility as a feedstock in making a variety of polymeric materials such as polypropylene that finds a number of uses in fabricated articles.

The heterogeneous catalysts provide an ethylene conversion of more than 90 mole percent (mol %), based upon total moles of ethylene in the feedstream, and a selectivity to $C_3$ oxygenates, preferably to propanol and propanal (propionaldehyde) of at least 70 mol % based upon total moles of product in the product stream. Selectivity to $C_3$ oxygenates preferably favors propanol over propanal such that the product stream contains more propanol than propanal.

The heterogeneous catalysts represented by general formula $Rh_aAg_bSn_cX_dY_eO_x$ have a Rh content that is within a range of from 0.1 mmol/hg to 50 mmol/hg, preferably from 5 mmol/hg to 30 mmol/hg, an Ag content that is within a range of from 0.1 mmol/hg to 50 mmol/hg, preferably from 2 mmol/hg to 10 mmol/hg, a Sn content that is within a range of from 0.1 mmol/hg to 50 mmol/hg, preferably from 0.8 mmol/hg to 5 mmol/hg, an X content that is within a range of from 0 mmol/hg to 222 mmol/hg, preferably from 1 mmol/hg to 40 mmol/hg, a Y content that is within a range of from 0 mmol/hg to 1500 mmol/hg, preferably from 1 mmol/hg to 500 mmol/hg, and an O content is decided by the net compound formed. Each mmol/hg is based upon combined weight of Rh, Ag, Sn, X, Y and O.

Arabic numerals designate Examples (Ex) of the present invention and capital alphabetic letters indicate Comparative Examples (Comp Ex or CEx).

68839 EXAMPLES

CEx A

In a 10 ml glass vial, add an aqueous solution (0.95 ml) containing 48.59 micromoles mol) (10.17 mg) $RhCl_3.3H_2O$ to 0.5 g of silica (Davison™57, surface area=280±20 m²/g) and stir the resultant mixture with a metal whisk at room temperature. Subject container contents to drying overnight at 120° C. (under vacuum?) Impregnate the dried contents with 0.475 ml of an aqueous solution containing 21.75 (µmol) (1.27 mg) NaCl. Dry the impregnated contents at room temperature for 4 hrs. Calcine dried container contents in air at 400° C. for 4 hrs in static air (heating rate of 2° C./minute) to yield a catalyst represented as $Rh_{9.718}Na_{4.35}/SiO_2$.

Evaluate catalyst performance using a high pressure parallel fixed bed reactor (PFBR) (PFBR System P/N; 132088 from Symyx™ Technologies Inc), a modular reactor composed of three bays, each of which contains 16 reactor tubes. The tubes in each bay are enclosed in a stainless steel bell jar capable of being pressurized with nitrogen ($N_2$) at the same pressure as that used in each reaction. Load reactor tubes with 200 microliters (µL) of catalyst, reduce the catalyst in situ at 35 bar (3.5 MPa) for three hours at 350° C. (heating rate of 5° C. per minute) using a gaseous mixture of 90 volume % (vol %) hydrogen ($H_2$) and 10 vol % $N_2$, each vol % being based on total gaseous mixture volume. Cool the catalyst to 280° C.

Test the catalyst at a pressure of 35 bar (3.5 MPa) and temperatures of 280° C., 300° C. and 320° C. using a feed mixture of 42.6 vol % $H_2$, 42.6 vol % CO, 4.8 vol % ethylene and 10 vol % $N_2$, each vol % being based on total feed mixture volume, flowing over the catalyst at a rate of 20.8 ml/minute. Maintain the temperature at 320° C., but increase the pressure to 90 bars (9 MPa) to evaluate a higher pressure. Increase the temperature to 340° C., but return the pressure to 35 bars (3.5 MPa) to evaluate a higher temperature. Evaluate reactor tube effluent using a Siemens process GC. Replicate this catalyst test cycle two additional times and report test results as an average of three test cycles in Table 1 below.

CEx B

Replicate CEx A, but substitute an aqueous solution (1 ml) that contains 23.18 µmol (3.94 mg) $AgNO_3$ and 19.11 µmol (5.68 mg) $Zn(NO_3)_2.6 H_2O$ for the aqueous solution that contains $RhCl_3.3H_2O$. The catalyst is represented as $Ag_{4.635}$—$Zn_{3.823}$—$Na_{4.35}/SiO_2$.

CEx C

Replicate CEx A with changes. First, impregnate the silica with an aqueous solution (1 ml) that contains 23.18 µmol (3.94 mg) $AgNO_3$ and dry it overnight at 120° C. Second, impregnate the dried, impregnated silica with 0.475 ml of an aqueous solution that contains 48.59 µmol (10.17 mg) of $RhCl_3.3 H_2O$ and dry it at 100° C. for 4 hrs. Third, impregnate the dried, twice impregnated silica with 0.475 ml of an aqueous solution that contains 21.75 µmol (1.27 mg) of NaCl to form a paste. Subject the paste to drying first under vacuum at 80° C. for 4 hours (hr) and then at 120° C. at atmospheric pressure for 4 hr. Calcine the dried paste as in CEx A to yield a catalyst represented as $Rh_{9.718}$—$Ag_{4.635}$—$Na_{4.35}/SiO_2$.

Ex 1

Replicate CEx C, but add 8.44 µmol (1.6 mg) of tin chloride ($SnCl_2$) to the aqueous solution that contains NaCl, to yield a catalyst represented as $Rh_{9.718}$—$Ag_{4.635}$—$Sn_{2.106}Na_{4.35}/SiO_2$.

Ex 2

Replicate Ex 1, but reduce the amount of $SnCl_2$ to 4.22 µmol (0.8 mg) and add 19.11 µmol (5.68 mg) of zinc nitrate hexahydrate ($Zn(NO_3)_2.6 H_2O$) to the aqueous solution that contains $AgNO_3$ to yield a catalyst represented as $Rh_{9.718}$—$Ag_{4.635}$—$Zn_{3.823}Sn_{0.842}Na_{4.349}/SiO_2$.

Ex 3

Replicate Ex 1, but add 51.43 µmol (13.19 mg) of magnesium nitrate hexahydrate $Mg(NO_3)_2.6 H_2O$ to the aqueous solution that contains $AgNO_3$ to yield a catalyst represented as $Rh_{9.718}$—$Ag_{4.635}$—$Zn_{3.823}Mg_{10.286}Sn_{0.842}Na_{4.349}/SiO_2$.

Ex 4

Replicate Ex 3 with changes. First, increase the amount of $AgNO_3$ to 34.77 µmol (5.91 mg). Second, increase the amount of $Zn(NO_3)_2.6 H_2O$ to 38.22 µmol (11.37 mg). Represent the catalyst as $Rh_{9.718}$—$Ag_{6.953}$—$Zn_{7.646}$—$Mg_{10.286}$—$Sn_{0.842}$—$Na_{4.349}/SiO_2$. See Table 2 for test results.

Ex 5

Replicate Ex 4, but increase the amount of $RhCl_3.3H_2O$ to 121.475 µmol (24.42 mg). The catalyst is represented as $Rh_{24.294}$—$Ag_{6.953}$—$Zn_{7.646}$—$Mg_{10.286}$—$Sn_{0.842}$—$Na_{4.349}/SiO_2$.

Ex 6

Replicate Ex 5 with changes. First, eliminate addition of the $Mg(NO_3)_2.6H_2O$. Second, after calcination, use a mortar and pestle to physically mix 502 mg of calcined, dried paste with 1.1 mg of sodium carbonate ($Na_2CO_3$). The physically mixed catalyst is represented as $Rh_{2.5}$—$Ag_{6.953}$—$Zn_{7.646}$—$Sn_{0.842}$—$Na_{4.349}$—$NC_{4.717}/SiO_2$. "NC" refers to sodium carbonate.

Ex 7

In a single neck glass reactor equipped with a stirring bar add aqueous solutions containing 0.0512 g $RhCl_3 \cdot 3H_2O$, 0.0076 g $SnCl_2 \cdot 2 H_2O$, 0.0157 g $AgNO_3$ and 0.0289 g of $Fe(NO_3)_3 \cdot 9H_2O$ to 2.0 g of $SiO_2$ support (Aerosil™ 300, Degussa, surface area=300±30 square meters per gram ($m^2$/g)) with constant stirring at room temperature (nominally 25° C.) for an hour. Raise the temperature and evaporate the contents of the reactor to dryness. Dry and calcine the evaporated powder as in CEx A to yield a silica-supported Rh catalyst represented as $Rh_{9.718}Sn_{1.685}Ag_{4.635}Fe_{3.581}/SiO_2$. See Table 3 for test results.

Ex 8

Replicate Ex 7 but replace the $Fe(NO_3)_3 \cdot 9H_2O$ with 0.013 g of $Mn(NO_2)_2$ to yield a catalyst represented as $Rh_{9.718}Sn_{1.685}Ag_{4.635}Mn_{3.64}/SiO_2$.

Ex 9

Replicate Ex 7 but replace the $Fe(NO_3)_3 \cdot 9H_2O$ with 0.0308 g of $Cr(NO_3) \cdot 9H_2O$ to yield a catalyst is represented as $Rh_{9.718}Sn_{1.685}Ag_{4.635}Cr_{3.846}/SiO_2$.

Ex 10

Replicate Ex 7 but replace the $Fe(NO_3)_3 \cdot 9H_2O$ with 0.0198 g of $Co(NO_3)_2 \cdot 6H_2O$ to yield a catalyst represented as $Rh_{9.718}Sn_{1.685}Ag_{4.635}Co_{3.394}/SiO_2$.

Ex 11

Replicate Ex 7 but replace the $Fe(NO_3)_3 \cdot 9 H_2O$ with 0.0070 g of $IrCl_4 \cdot x H_2O$ to yield a catalyst represented as $Rh_{9.718}Sn_{1.685}Ag_{4.635}Ir_{1.04}/SiO_2$.

TABLE 1

| Ex. No. | Temperature, C | X(ethylene), % | S(Propanal + Propanol), % | S(Ethane), % |
|---|---|---|---|---|
| D | 300 | 10.2 | 49.8 | 46.2 |
| E | 300 | 0.4 | 7.7 | 92.3 |
| F | 300 | 4.5 | 39.2 | 54.4 |
| 1 | 300 | 6.5 | 39.4 | 58.6 |
| 2 | 300 | 17.5 | 53.6 | 46.1 |
| 3 | 300 | 19.4 | 59.6 | 39.4 |
| D | 320 | 12.2 | 47.9 | 45.8 |
| E | 320 | 0.7 | 19.1 | 80.9 |
| F | 320 | 8.8 | 40.3 | 53.7 |
| 1 | 320 | 10.5 | 34.6 | 61.3 |
| 2 | 320 | 30.7 | 50.1 | 48.0 |
| 3 | 320 | 33.9 | 56.6 | 41.7 |
| D | 340 | 21.9 | 40.9 | 46.6 |
| E | 340 | 0.1 | 27.6 | 72.4 |
| F | 340 | 44.6 | 26.8 | 67.0 |
| 1 | 340 | 11.2 | 29.3 | 63.0 |
| 2 | 340 | 44.6 | 49.1 | 49.1 |
| 3 | 340 | 53.2 | 54.4 | 44.2 |

X* means conversion;
S** means selectivity

TABLE 2

| Ex. No. | Temperature, C | Pressure, bar | X(ethylene), % | S(Propanal + Propanol), % | S(Ethane), % |
|---|---|---|---|---|---|
| 4 | 280 | 35 | 8.8 | 56.1 | 43.9 |
| 4 | 300 | 35 | 17.1 | 53.8 | 45.7 |
| 4 | 320 | 35 | 28.4 | 47.7 | 50.9 |
| 4 | 320 | 90 | 43.0 | 60.7 | 37.9 |
| 4 | 340 | 35 | 47.3 | 45.9 | 52.9 |
| 5 | 300 | 35 | 26.9 | 50.7 | 48.2 |
| 5 | 320 | 35 | 49.5 | 47.2 | 50.9 |
| 5 | 340 | 35 | 86.8 | 45.8 | 52.4 |
| 6 | 300 | 35 | 16.7 | 46.8 | 53.2 |
| 6 | 320 | 35 | 28.5 | 44.6 | 55.0 |
| 6 | 340 | 35 | 46.4 | 46.1 | 50.8 |

X* means conversion;
S** means selectivity.

TABLE 3

| Ex. No. | Temperature, C | Pressure, bar | X(ethylene), % | S(Propanal + Propanol), % | S(Ethane), % |
|---|---|---|---|---|---|
| 7 | 280 | 35 | 61.1 | 20.7 | 50.5 |
| 8 | 280 | 35 | 79.6 | 22.9 | 41.2 |
| 9 | 280 | 35 | 70.9 | 22.2 | 42.7 |
| 10 | 280 | 35 | 63.5 | 14.7 | 49.3 |
| 11 | 280 | 35 | 58.3 | 39.4 | 5.1 |

X* means conversion;
S** means selectivity, GHSV = 6730 $h^{-1}$.

The data in Tables 1-3 demonstrate that catalyst compositions comprising, consisting essentially of or consisting of Rh, Ag and Sn show efficient for conversion of a feed that contains ethylene, carbon monoxide and hydrogen to produce at least C3 oxygenates. The data also show that catalyst performance improves when the catalyst further comprises one or more additional elements selected from a group consisting of Zn, alkali metals, alkaline earth metals, and transition metals. Preferred transition metals include iron, manganese, chromium, cobalt and iridium.

What is claimed is:

1. A process for converting a feedstream comprising syngas and ethylene to a product stream that comprises at least one three carbon oxygenate, which process comprises placing the feedstream in contact with a heterogeneous catalyst under conditions sufficient to effect conversion of the feedstream to the product stream, the catalyst comprising a combination of metals on a catalyst support, the combination of metals being represented by general formula $Rh_aAg_bSn_cX_dY_eO_x$ wherein X is at least one transition element other than rhodium or silver, Y is at least one element selected from alkali metals and alkaline earth metals, a is a real number within a range of from 0.1 millimole/hectogram to 50 millimole/hectogram, b is a real number within a range of from 0.1 millimole/hectogram to 50 millimole/hectogram, c is a real number within a range of from 0.1 millimole/hectogram to 50 millimole/hectogram, d is a real number within a range of from 0 millimole/hectogram to 250 millimole/hectogram, e is a real number within a range of from 0 millimole/hectogram to 1500 millimole/hectogram, and x is a real number greater than zero needed to balance the total charges of Rh, Ag, Sn, X and Y elements, the catalyst support being at least one of silica, alumina, titania, magnesia, magnesium aluminate, and zinc aluminate.

2. The process of claim 1, wherein X is at least one element selected from a group consisting of zinc, iron, manganese, chromium, cobalt and iridium.

3. The process of claim 1, wherein the conditions include at least one of a temperature within a range of from 100° C. TO 450° C., a pressure within a range of from 12 pounds per square inch gauge (psig) (82.7 kilopascals (KPa)) to 4,000 psig (27.6 megapascals (MPa)), a gas hourly space velocity (GHSV) within a range of from 25 reciprocal hours ($h^{-1}$) to 25,000 $h^{-1}$, and a feedstream ratio of ethylene to carbon monoxide to hydrogen ($C_2H_4$:CO:$H_2$) within a range of from 0.01:10:10 to 10.0:0.01:0.01.

* * * * *